United States Patent [19]

Kucey

[11] Patent Number: 5,026,417
[45] Date of Patent: Jun. 25, 1991

[54] METHODS AND COMPOSITIONS FOR INCREASING THE AMOUNTS OF PHOSPHORUS AND/OR MICRONUTRIENTS AVAILABLE FOR PLANT UPTAKE FROM SOILS

[75] Inventor: Reginald M. N. Kucey, Alberta, Canada

[73] Assignee: Her Majesty the Queen in right of Canada, as represented by the Minister of Agriculture, Canada

[21] Appl. No.: 488,944

[22] Filed: Mar. 5, 1990

Related U.S. Application Data

[63] Continuation of Ser. No. 293,758, Jan. 5, 1989, abandoned, which is a continuation-in-part of Ser. No. 167,035, Mar. 11, 1988, abandoned.

[30] Foreign Application Priority Data

Mar. 17, 1987 [CA] Canada ................................. 532255
Jul. 22, 1987 [CA] Canada ................................. 542706
Dec. 24, 1987 [CA] Canada ................................. 555378

[51] Int. Cl.$^5$ ......................... C05B 21/00; C05G 3/00
[52] U.S. Cl. .............................................. 71/35; 71/6; 71/32; 435/254; 435/933; 47/57.6
[58] Field of Search .................. 71/6, 32, 35, 902; 435/259, 933; 47/57.6

[56] References Cited

PUBLICATIONS

Mycologia, vol. 76, No. 3, 1984, Shechau et al., "Spore Germination & Microcycle Conidiation of Two Pencillia in Soil".

*Primary Examiner*—Ferris H. Lander

[57] ABSTRACT

A method and composition for increasing the amounts of phosphorus and/or micronutrients available for uptake by plants from the soil. The invention involves introducing an inoculum of the fungus *Penicillium bilaji* into (or onto) the soil. This has the effect of increasing the solubility of phosphates and micronutrient sources which may be either native to the soil or added to it, e.g. in the form of insoluble rock phosphate or manufactured phosphate fertilizer. The invention can be used to increase the health, growth rates and yields of plants, especially crop plants grown on nutrient-deficient soils, while eliminating or minimizing the need for expensive manufactured fertilizers.

40 Claims, No Drawings

METHODS AND COMPOSITIONS FOR INCREASING THE AMOUNTS OF PHOSPHORUS AND/OR MICRONUTRIENTS AVAILABLE FOR PLANT UPTAKE FROM SOILS

RELATED APPLICATIONS

This is a continuation of our co-pending U.S. patent application Ser. No. 293,758 filed on Jan. 5, 1989 (now abandoned), which is itself a continuation-in-part of our co-pending U.S. patent application Ser. No. 167,035 filed on Mar. 11, 1988 now abandoned.

BACKGROUND OF THE INVENTION

I. Field of the Invention

This invention relates to methods and compositions for increasing the amounts of phosphorus and/or micronutrients available for uptake by plants from soils.

II. Description of the Prior Art

In order to maintain healthy growth, plants must extract a variety of elements from the soil in which they grow. These elements include phosphorus and the so-called micro-nutrients (e.g. copper, iron and zinc), but many soils are deficient in such elements or they contain them only in forms which cannot be readily taken up by plants (it is generally believed that essential elements cannot be readily taken up by plants unless they are present in dissolved form in the soil).

To counteract such deficiencies, sources of the deficient elements are commonly applied to soils in order to improve growth rates and yields obtained from crop plants. For example, phosphates are often added to soil to counteract a lack of phosphorus. Large deposits of rock phosphates are available in many locations, but untreated rock phosphates have low water (citric acid) solubilities, particularly in neutral or alkaline soil systems, and consequently do not provide an easily-assimilable source of phosphorus. In order to overcome this problem, rock phosphates are usually chemically converted to more soluble compounds (e.g. mono-ammonium phosphate or triple-super-phosphate) in large-scale fertilizer-manufacturing facilities. However, such conversions suffer from the disadvantages that they are relatively expensive and the conversion facilities may not be conveniently located close to crop-growing areas.

Attempts have been made in the past to use microorganisms to improve the availability of essential elements in soil systems. For example, known phosphorus-solubilizing bacteria and actinomycetes have been added to soil to increase the levels of available phosphorus. However, such techniques have not found widespread acceptance, perhaps because the microorganisms were not effective at solubilizing phosphorus in soil or perhaps because their methods of application were difficult or inconvenient.

Accordingly, there is a need for an improved system for increasing the levels of available phosphorus and/or micro-nutrients in soil systems, and particularly in neutral or alkaline soil systems.

SUMMARY OF THE INVENTION

The present invention is based on the finding that a particular fungus, *Penicillium bilaji*, not only has a very good ability to improve the availability of phosphorus both from insoluble phosphates and from manufactured fertilizers and that it can also improve the availability of micronutrients such as copper and zinc, but also that the fungus propagates readily and remains viable when applied to soils and so can be used without difficulty as a soil amendment.

The fungus can be applied to soils which already contain insoluble phosphates or micronutrients, or it can be applied in conjunction with untreated rock phosphates or manufactured fertilizers.

Thus, according to one aspect, the invention provides a method of increasing the availability of phosphorus and/or micronutrients for plant uptake from soil, which method comprises introducing into the soil an inoculum of the fungus *Penicillium bilaji* to release for plant uptake said phosphorus and/or micronutrients from a source thereof originally present in the soil or added thereto as an amendment.

According to another aspect of the invention, there is provided a composition for application to soil, which comprises an inoculum of the fungus *Penicillium bilaji* and a soil-compatible carrier for the fungus.

Other aspects of the invention relate to plant seeds coated with the fungus and to a novel strain of the fungus itself.

The term "inoculum" as used in this specification is intended to mean any form of fungus cells or spores which is capable of propagating on or in the soil when the conditions of temperature, moisture, etc., are favourable for fungal growth.

The term "soil-compatible" means any material which can be added to the soil without having an adverse effect on plant growth, soil structure, soil drainage or the like.

By "source" of a particular element we mean a compound of that element which, at least in the soil conditions under consideration, does not make the element fully available for plant uptake.

The use of the fungus *P. bilaji* can, at least according to the preferred embodiments of the invention, have the following advantages. When applied to soil already containing insoluble (or sparingly soluble) phosphates, the use of the fungus can result in an increase in the yield of plants grown in the soil. The fungus also enables insoluble rock phosphates to be used as an effective fertilizer for soils which have inadequate amounts of available phosphorus. Furthermore, the use of the fungus in conjunction with many manufactured phosphorus fertilizers enables the amount of the fertilizer to be reduced without reducing the yield and health of the plants.

DETAILED DESCRIPTION OF THE INVENTION

The fungus *Penicillium bilaji* is a known micro-organism that has previously been deposited at the American Type Culture Collection in Rockville, Md., USA under the deposit number ATCC 22348 (1974 edition of the ATCC catalogue). In the 1984 catalogue, the same deposit number is used for *P. bilaii* and a further strain is identified by the deposit number 18309. It is not known whether the change of name occurred as a result of a clerical error or whether the fungus has been re-named. In any event, the name *P.bilaji* is used for the microorganism throughout this specification.

The inventor has discovered a further strain of the micro-organism in soil from a location (latitude 49° 48′ N, longitude 113° 6′ W) in Southern Alberta, Canada. This strain has improved P-solubilizing activity compared to the strains previously deposited at the ATCC.

A deposit of the improved strain has been made at the ATCC under the deposit number 20851 in accordance with the terms of the Budapest Treaty.

The taxonomic details of our new strain are as follows:

| Czapek Yeast Extract Agar (CYA) | |
|---|---|
| (25° C., 7 days): | 26.2 mm diam.; wide margin deep; dense; plane to radially sulcate; floccose to funiculose; |
| mycelium: | white |
| condidia: | dull green (Methuen 25-27 D3) |
| exudate: | present, clear to amber |
| sol. pigment: | brown |
| reverse: | reddish brown (M9E-P8) |
| Malt Extract Agar | |
| (25° C., 7 days): | 20-25 mm diam.; margin low and wide; low to medium; medium; plane; velutinous to floccose to funiculose; |
| mycelium: | inconspicuous |
| condidia: | dull green (Methuen 25-27 D3) |
| exudate: | absent |
| sol. pigment: | brown |
| reverse: | pale |
| 25% Glycerol Nitrate Agar | |
| (25° C., 7 days): | 13-16 mm diam.; plane to radially sulcate; floccose; |
| mycelium: | white |
| condidia: | sparse, similar to CYA at 25° C. |
| exudate: | absent |
| sol. pigment: | brown |
| reverse: | pale |
| CYA at 5° C.: | 0 i.e. no germination/growth |
| CYA at 37° C.: | 10-15 mm diam; convolute, margin irregular; velutinous; |
| mycelium: | white |
| exudate: | absent |
| sol. pigment: | brown |
| reverse: | brown |
| C'PHORES: | Solitary aerial |
| STIPES: | length: 30-100 μm walls: smooth |
| PENICILLI: | monoverticillate: vesiculate |
| PHIALIDES: | ampulliform; no.: 10+ 6-8 μm long collula: short |
| CONIDIA: | subspherical; well-defined columns; 2.5-3 μm long; finely rough |

The fungus can be easily propagated on a suitable carbon source such as autoclaved moist ground wheat straw amended with glucose, unamended bran, etc. Propagation normally takes place for a period of about one week or more before the inoculum is ready for use. The resulting fungus propagated on a solid support may be used as such for incorporation into soil, most preferably at the root level, but may be coated onto the seeds if desired. Alternatively, a liquid culture of the fungus may be prepared by using a conventional nutrient solution. The liquid culture may then be used as such or dried and the dried product applied to the soil either with or without a suitable carrier and/or nutrient source.

It has also been found that starch, cellulose and mixtures thereof are suitable carriers for the fungal spores. These materials make it easy to handle the spores and also act as carbon sources for the spores.

The spores can simply be mixed with the carrier (e.g. a 50:50 by weight mixture of soluble starch and cellulose) and then the spore content can be adjusted, if desired, by the addition of further carrier.

The spore/carrier mixture can be added to a seed row of the soil at the root level or can be used to coat seeds prior to planting. When used to coat seeds, the spore/-carrier mixture can simply be mixed with water, applied to the seeds and allowed to dry.

Other carriers for the spores can be used to coat seeds. For example, the spores can be grown on moistened bran, dried, sieved and applied to seeds prior coated with an adhesive, e.g. gum arabic.

The amount of the inoculum to be applied to the soil is not limited in any particular respect. Clearly, if insufficient is used, a noticeable effect will not be obtained. On the other hand, the use of large amounts of the inoculum will be wasteful because the amounts of phosphorus and/or micronutrients made available in the soil reach a maximum at a certain application rate and further additions beyond this rate do not give additional benefits. The suitable application rates vary according to the type of soil, the type of crop plants, the amounts of the source of phosphorus and/or micronutrients present in the soil or added thereto, etc. and a suitable rate can be found without difficulty by simple trial and experiment for each particular case. Normally, the application rate falls into the range of 0.001–1.0 Kg fungal spores and mycelium (fresh weight) per hectare, or $10^2$–$10^6$ colony forming units (cfu) per seed (when coated seeds are used, or a few grams of inoculated carrier (containing up to about $9 \times 10^{10}$ cfu/g) per meter of plant row.

Since the fungus has the effect of solubilizing phosphates and micronutrients which may already be present in soil (i.e. those which are native to the soil) and also those which are added to the soil, the fungus may be applied alone to soils which contain native sources of phosphorus and/or micronutrients, or may be applied to any soils in conjunction with added sources of phosphorus and/or micronutrients.

Untreated rock phosphate is not only a source of phosphorus, but also usually contains micronutrients (e.g. copper, iron and zinc). Accordingly, the use of *P. bilaji* in conjunction with added or native rock phosphate forms a particularly preferred aspect of the invention because both phosphorus and micronutrients are made available for plant uptake in this way. Manufactured fertilizers often contain such sources and so the double benefit of the invention is also obtained when these fertilizers are used with the *P. bilaji*. If the phosphorus source does not contain the micronutrients, sparingly soluble sources of these elements may be added to the soil with the *P. bilaji*. However, other sources of phosphorus which occur naturally in soil or are added thereto may be used.

As noted above, it has surprisingly been found that the fungus increases the amount of phosphorus available for plant uptake from commercial phosphorus fertilizers, thus reducing the amounts of these fertilizers required, so commercial fertilizers may be added to the soil instead of (or even as well as) natural rock phosphate.

It is theorized that the fungus increases the amount of phosphorus available for plant uptake from commercial phosphorus fertilizers because these fertilizers are acted upon by soil components in such a way as to convert a certain proportion of the phosphorus into insoluble phosphorus compounds and this proportion is then solubilized by the action of the fungus and hence does not go to waste.

Commercially available phosphate fertilizers are of many types. Some common ones are those containing monoammonium phosphate (MAP), triple super phosphate (TSP), diammonium phosphate, ordinary superphosphate and ammonium polyphosphate. All of these fertilizers are produced by chemical processing of insoluble natural rock phosphates in large scale fertilizer-manufacturing facilities and, as noted above, the product is expensive. By means of the present invention, at least in its preferred forms, it is possible to reduce the amount of these fertilizers applied to the soil by up to 50% or more while still maintaining the same amount of phosphorus uptake from the soil. Bearing in mind that recent statistics have shown that expenditures for processed phosphate fertilizers in the three prairie provinces of Canada alone are roughly 75 million dollars per year, the use of the present invention has the potential for generating significant savings.

When pulverized rock phosphate is used as the source of phosphorus and/or micronutrients, the supported fungus may be mixed with pulverized rock phosphate and the resulting mixture introduced into the soil, preferably at the root level, or alternatively the fungus may be added to the soil separately from the rock phosphate. When a manufactured fertilizer is used as a phosphorus source, it cannot be mixed with the supported fungus because the salt effect of the concentrated fertilizer weakens or destroys the fungus inoculum. The inoculum and manufactured fertilizer should also be prevented from coming into contact in the soil, e.g. by providing a soil layer between the fertilizer and the inoculum.

Other fertilizers, such as nitrogen sources, or other soil amendments may of course also be added to the soil at approximately the same time as the supported fungus or at other times, so long as the other materials are not toxic to the fungus.

Preferably, a carbon source for fungal growth such as ground straw (e.g. wheat straw) or bran is applied to the soil in addition to the phosphate and $P.$ $bilaji$. This carbon source may be additional to the one used for the initial propagation of the fungus, i.e. the one forming part of the inoculum. The additional carbon source often increases the nutrient uptake of plants grown in the soil, presumably because of increased fungal growth rates.

It has been found that the presence of a small amount of nitrogen (introduced in the form of the ammonium ion) improves the P-solubilizing activity of $P.$ $bilaji$. For this reason $NH_4Cl$ or another ammonium source is preferably applied to the soil at approximately the same time as, or in admixture with, the supported fungus. The amount of the ammonium source added normally falls within the range of 5-20 Kg N/ha. When a manufactured fertilizer such as MAP is added to the soil, the ammonium need not be added because it is already a component of the fertilizer.

The mechanism by which $P.$ $bilaji$ solubilizes insoluble phosphate is not precisely known. However, it is theorized that the fungus may operate via two separate mechanisms, one requiring the presence of the ammonium ion and a second which does not involve ammonium, and involves the excretion of organic acids. The mechanism by which $P.$ $bilaji$ makes micronutrients available for plant uptake is thought to be through excretion of organic acids.

It has been found that the presence of vesicular-arbuscular mycorrhizal fungi (hereinafter referred to as VAM) in the root zone is necessary for good P-uptake, but such micro-organisms are normally present in soil, so specific addition of such micro-organisms is not required unless they are absent from the soil or present only in unusually small amounts.

The invention is illustrated in more detail by the following Examples. In Examples 1 to 12, the $P.$ $bilaji$ strain employed for the tests was the deposited ATCC 20851 strain. Example 13 illustrates and compares the effectiveness of the ATCC 22348, 18309 and 20851 strains.

EXAMPLE 1

In this Example, the effect of the invention was assessed on plants growing in a greenhouse.

A Brown Chernozemic soil (loamy sand, Cavendish series) was collected from a cultivated field near Iron Springs, Alberta. The soil was air-dried, sieved (2 mm) and mixed with an equal volume of sand. The final mixture had a pH of 7.2 (measured after mixing with an equal volume of water) contained 1.8% organic matter and contained 2 $\mu g$ of available phosphorus per gram of soil ($NaHCO_3$-ext, Olsen et. al., 1954). One kg of the soil was added to 20 cm ceramic pots.

The soils in different pots were provided with different amendments, as shown in Table 1.

The fertilizer materials used in these tests are described in more detail below.

The Idaho rock phosphate (containing 10.3% by weight P) was sieved and the fine material used in an amount equivalent to 90 Kg P/ha.

The triple-super-phosphate (TSP) was added to the pot at a rate equal to 30 Kg P/ha.

Wheat straw was ground to an average particle size of about 2 mm and added to the pot in an amount equal to 1000 Kg/ha. Rock phosphate was thoroughly mixed with the straw when both materials were used.

$P.$ $bilaji$ was grown on autoclaved ground wheat straw amended with 1.0% by weight glucose for 2 weeks, at which time the straw particles were covered with $P.$ $bilaji$ spores. The $P.$ $bilaji$ inoculum used in the tests consisted of 0.1 g/pot of moist colonized straw particles. The inoculum was placed on top of the straw in the pots when both were employed.

The various amendments were added to the soil in the pots and seeds were planted in the soil in the following manner.

All of the soil amendments were then placed at the bottom of a 5 cm deep hole dug in the centre of each pot and soil was then placed over them. Seeds were planted in the area between the center hole and the side of the pots. An amount of $NH_4Cl$ equal to 23.5 Kg N/ha was added to the holes below the seeds in each pot. An amount equal to 75 Kg N/ha of nitrogen fertilizer ($NH_4NO_3$) was added to the surface of the soil of each pot. Five wheat seeds (*Triticum aestivum* var. Chester) or four bean seeds (*Phaseolus vulgaris* var. GN1140) were planted in each pot and later thinned to two plants per pot. Each of the bean seeds were inoculated with a commercial *Rhizobium phaseoli* inoculant (from Nitragin Co.). The treatments shown in Table 1 was used for both test crops. Pots containing wheat received a further amount of N equal to 60 Kg N/ha at the beginning of week four of growth.

Five replicates of each treatment for each test crop were randomly arranged on greenhouse tables. The arrangement of the pots was altered every two weeks for the duration of the experiment. Supplemental lighting was used to maintain a 16 yr/8 hr day/night cycle. Phosphorus-free Long-Ashton nutrient solution (20 ml) was added to each pot on growth weeks 2, 3 and 8.

The plants were harvested at maturity, dried, weighed and ground. Subsamples of the plant material were acid-digested and analyzed for P-content.

Statistical analysis of the data was performed using a General Linear Model program of a Statistical Analysis Systems package. Least significant differences were calculated from the General Linear Model procedure. Single degree of freedom comparisions were made between individual treatments to determine differences or lack of differences.

The results of the tests are shown in Table 1 below.

TABLE 1

| Soil Sample | Dry Matter (g/pot) | | P Content (mg/Pot) | |
|---|---|---|---|---|
| | Wheat | Beans | Wheat | Beans |
| Idaho Rock Phosphate | 2.4 | 4.6 | 3.6 | 7.2 |
| P. bilaji | 2.5 | 4.5 | 4.3 | 7.3 |
| P. bilaji + Rock P. | 2.5 | 4.9 | 4.0 | 7.5 |
| STRAW + Rock P. | 2.3 | 4.3 | 3.5 | 6.9 |
| STRAW + P. bilaji | 2.8 | 5.2 | 4.3 | 8.0 |
| STRAW + P. bilaji + Rock P. | 3.2 | 5.6 | 5.1 | 8.6 |
| Triple Super Phosphate | 2.7 | 6.1 | 4.8 | 10.1 |
| Unfertilized Control | 2.3 | 3.6 | 3.9 | 6.6 |
| Least Significant Difference (p < 0.05) | 0.3 | 0.9 | 1.0 | 1.6 |

Statistical Analysis (Single degree of freedom comparisons)

| Contrast | | | | | |
|---|---|---|---|---|---|
| S + R + P vs TSP | 1 | 0.4* | 0.8 | 0.2 | 5.8 |
| S + R + P vs Cont | 1 | 2.0** | 9.5** | 6.2* | 9.8* |
| S + R + P vs S + R | 1 | 2.0** | 3.9** | 5.9* | 7.5* |
| S vs noS## | 1 | 0.4* | 3.3* | 1.2 | 7.3* |
| S + P vs Cont | 1 | 0.5* | 5.4** | 1.5 | 2.8 |
| P vs Cont | 1 | 0.8** | 1.6 | 7.2* | 0.1 |
| S + R vs Cont | 1 | 0.1 | 1.2 | 0.4 | 0.1 |
| R vs Cont | 1 | 0.1 | 0.1 | 0.9 | 3.0 |

S = straw;
R = rock phosphate;
P = Penicillium;
Cont = control;
TSP = triple superphosphate
All treatments with straw vs equivalent treatments without straw
*Effect significant at P < .05
**Effect significant at P < .01

The data shows that for both dry matter production (DMP) and P uptake, treatment with straw + rock phosphate + P. bilaji resulted in significantly higher levels than the unfertilized control and also higher than the treatment receiving only straw and rock phosphate. Addition of rock phosphate alone or in combination with straw in the absence of P. bilaji did not have a significant effect on DMP or P-uptake of either crop plant. The addition of P. bilaji alone had a positive effect on wheat DMP and P-uptake, but did not affect these parameters for beans. Addition of P. bilaji plus straw increased wheat and bean DMP, but did not affect the P-uptake of either crop.

The addition of straw in combination with the other amendments had a significant positive influence on the effectiveness of those treatments.

When compared to the effectiveness of triple-superphosphate, the straw + rock phosphate + P. bilaji treatment was not significantly less effective for bean DMP and P-uptake by wheat or beans. The complete treatment was significantly more effective than triple-superphosphate in the case of wheat DMP.

EXAMPLE 2

In this Example, the effect of the invention was assessed on plants growing in an outdoor field during 2 growing seasons.

Adjacent plots of land were selected on the Vauxhall substation of the Lethbridge Research Station, Alberta. The soil was an Orthic Brown Chernozem, clay-loam texture, contained 3.5% organic matter and contained 2 $\mu g$ $NaHCO_3$-ext P/g soil. The treatments used in the field experiments are shown in Tables 2 and 3.

The preparation of the rock phosphate, P. bilaji and straw were the same as in Example 1. Mono-ammonium phosphate (MAP) was used instead of triple-superphosphate.

Each treatment plot measured 2.0 m long and five rows (spaced 23 cm apart) wide. The furrows were hand dug 5 cm deep and the amendments hand-spread evenly along the length of the furrow. A separate subsample of material was weighed out for each row of a plot. Both rock phosphate and MAP were added to the soil at a rate equivalent to 18.1 Kg P/ha, which was the recommended rate of P addition for wheat in this soil. Straw was added at a rate equal to 87 Kg/ha. P. bilaji inoculum (spores, mycelium and straw combination equal to 43 Kg/ha fresh weight) was added per row. All the amendments added to a row were thoroughly mixed before addition to the soil. Wheat seed (Triticum aestivum var Chester) was spread along the row to provide 1 seed/2 cm row. Ammonium chloride was added to all rows except those containing MAP to equalize the N applied in the row. The furrows were covered over by hand and N as $NH_4NO_3$ was spread over the plot surface at a rate equal to 30 Kg N/ha in the first year and 60 Kg N/ha in the second year.

Five replicates of the ten treatments used in the first year and 10 replicates of the 7 treatments used in the second year were arranged in a randomized block design. The plots were irrigated as needed to maintain soil moisture tension below 450 KPa. The plants were harvested at maturity. Only the central 1.3 m of the central 3 rows of each plot were harvested. Dry matter weights of straw and seed were measured. The grin and straw from each plot was ground and combined and thoroughly mixed. The phosphorus content of the combined sample was measured following acid digestion. Statistical analysis was carried out as in the Example 1.

The results of the tests are shown in Tables 2 and 3.

TABLE 2

| | Grain (g/0.9 m$^2$) | Straw (g/0.9 m$^2$) | Total P. Uptake (g/0.9 m$^2$) |
|---|---|---|---|
| Rock Phosphate (RP) | 167 | 204 | 0.73 |
| P. bilaji + RP | 198 | 223 | 0.82 |
| Straw (S) | 151 | 192 | 0.69 |
| P. bilaji + S | 188 | 232 | 0.87 |
| RP + S | 185 | 224 | 0.84 |
| P. bilaji + S + RP | 232 | 303 | 1.10 |
| Mono-Ammonium Phosphate | 238 | 296 | 1.12 |
| Mono-Ammonium Phosphate + P. bilaji | 231 | 285 | 1.09 |
| Control | 163 | 202 | 0.71 |
| P. bilaji | 207 | 237 | 0.95 |
| Tukey's HSD | 48 | 90 | .26 |

Statistical Analysis (Single degree of freedom comparisons)

| Contrast | | | | |
|---|---|---|---|---|
| S + R + P vs Cont | 1 | 11764** | 25401** | 0.38** |
| S + R + P vs MAP | 1 | 90 | 130 | 0.01 |
| S + R + P vs S + R | 1 | 5429** | 15840** | 0.16** |
| S + R + P vs R + P | 1 | 2856** | 15920** | 0.19** |
| R + P vs Cont | 1 | 3028** | 1103 | 0.03 |
| P vs Cont | 1 | 3808** | 3478 | 0.14** |
| R vs Cont | 1 | 40 | 10 | 0.01 |

TABLE 2-continued

| | Grain (g/0.9 m$^2$) | Straw (g/0.9 m$^2$) | Total P. Uptake (g/0.9 m$^2$) |
|---|---|---|---|
| MAP + P vs MAP 1 | 130 | 314 | 0.01 |

S = Straw;
R = Rock phosphate;
P = P-solubilizing *Penicillium bilaji*;
Cont = control;
MAP = Mono-ammonium phosphate
**Effect significant at $P < .01$ The results for the first year show that grain and straw DMP were increased 1.4 and 1.5 times, respectively, as a result of the addition of straw+rock phosphate+*P. bilaji* to the soil. The increase was equivalent to that observed from the addition of MAP at equal rates of P, and greater than that observed from the addition of straw+rock phosphate. Addition of *P. bilaji* alone or in combination with straw or RP also had a significant effect on grain and straw DMP.

Inclusion of straw as a carbon source for fungal growth was shown to increase significantly the effectiveness of the rock phosphate+*P. bilaji*. The addition of *P. bilaji* to MAP did not affect grain or straw yields above the level of MAP alone. Rock phosphate addition alone or with straw did not have a significant effect.

Phosphorus uptake was increased by the addition of straw+rock phosphate+*P. bilaji* or the addition of MAP to the soil (1.5 times greater P than control for straw+rock phosphate+*P. bilaji*, 1.6 times greater than control for MAP). The straw+rock phosphate+*P. bilaji* and MAP treatments were not significantly different in their ability to affect P uptake. As with the DMP responses, the addition of *P. bilaji* to the straw+rock phosphate treatment increased the effectiveness of that combination. The addition of *P. bilaji* alone had a significant effect on phosphorus uptake, but when added with rock phosphate in the absence of straw, did not have an effect. Rock phosphate added alone or with straw did not significantly affect phosphorus uptake by the crop.

The results for the second year of the field study are shown in Table 3. In this experiment, *P. bilaji* inoculum was grown on moistened wheat bran.

TABLE 3

| Treatment | Dry Matter grain (Kg/ha) | Production straw (Kg/ha) | Total P Uptake (Kg/ha) |
|---|---|---|---|
| *P. bilaji* + RP + Straw | 3003 | 5825 | 12.18 |
| *P. bilaji* + RP | 3012 | 5839 | 12.09 |
| RP + Straw | 2501 | 5074 | 10.63 |
| *P. bilaji* | 2870 | 5826 | 12.33 |
| Rock P | 2709 | 5630 | 11.18 |
| Control | 2619 | 5494 | 10.76 |
| Mono-Amm. P. | 3025 | 6083 | 14.14 |
| Tukey's HSD ($p < .05$) | 342 | 613 | 0.88 |

| Analysis of Data with and without *P. bilaji* and MAP** | | |
|---|---|---|
| | Total Dry Matter | Total P |
| + *P. bilaji* | a | b |
| − *P. bilaji* | b | c |
| MAP | a | a |

**averages of all treatments receiving or lacking PSMO or receiving mono-ammonium phosphate.

These results from the second year of the field conducted study show again the effectiveness of the P-solubilizing fungus on the uptake of P from soil and from rock phosphate. The added straw did not increase the effectiveness of the system as was found for the first year of the study. The response for grain production was as great for the RP+*P. bilaji*+straw treatment when compared to MAP as the previous year, however the P uptake response was lower than from MAP. The results also show the effect of the fungus in the absence of added rock P in that the uptake of soil P was increased.

With respect to grain yield, the treatment with *P. bilaji*+RP+Straw was equivalent the MAP treatment. The *P. bilaji*+RP treatment was also equal in grain production. The *P. bilaji* and the RP treatments were lower than the MAP, or *P. bilaji*+RP with and without straw, but were not significantly different from them. Data analysis did show that treatments lacking *P. bilaji* were significantly less in dry matter production than those receiving MAP or *P. bilaji*.

EXAMPLE 3

In this Example, the effects of the invention were assessed under greenhouse conditions employing rock phosphate as the phosphorus source and spring wheat as the subject plant.

Soil (⅓ D. Brown Chernozemic soil, ⅔ sand pH=7.1, Org. matter=1.8%) was placed in several 6 inch diameter plastic pots and the pots were divided into four groups. Rock phosphate alone was added to the first group (equal to 103 Kg P/ha). *P. bilaji* inoculum alone was added to the second group (4.0 g fresh weight/pot). Rock phosphate and *P. bilaji* were both added to the third group at the rates used individually for groups 1 and 2. The fourth group of pots formed a control and nothing was added to the soil. (Test design: 4 plots×4 replicates).

Seeds of Chester spring wheat were added to each pot (10 seeds/pot, 1 inch deep, in direct contact with treatment). NH$_4$Cl was added to each pot (equal to 100 Kg N/ha). Water was added as required.

The plants were allowed to grow under identical conditions for 57 days and were then harvested. The plant height was recorded at harvest and the top growth was removed, dried for 72 hours at 60° C. and the dry weights recorded. The samples were ground in a Wiley (trade mark) mill grinder to approximately 2 mm.

The root micro-organisms and the total phosphate solubilizing micro-organisms were determined as follows.

Two 5.0 g samples of roots and rhizosphere soil were collected from each pot at harvest. Each sample was processed in a Waring (trade mark) blender for two minutes, then serially diluted in phosphate saline buffer. Total fungi and total phosphate solubilizing fungi counts were determined from PDA precipitated phosphate+0.003% streptomycin sulfate+0.007% rose bengal plates at 10$^7$, 10$^6$ and 10$^5$ dilutions. Total micro-organism counts were determined from PDA plates at 10$^9$, 10$^8$ and 10$^7$ dilutions. Counts from plates were carried out after 9–10 days.

The available phosphate in the soil was determined by the NaHCO$_3$ extract method (Jackson M. L., 1958, soil Chemical Analysis, pp 134–182).

The phosphorus content of plants was determined by the method of Olsen and Sommers (Olsen S. R. and Sommer, L. E., 1982, Methods of Soil Analysis, Part 2, pp 413–414).

The results are shown in Table 4 below:

TABLE 4

| Treatment | Plant Wt. (g/pot) | Plant Nutrients (/pot) | | | | | Soil Available P ($\mu g/g$) | P-Solubilizing fungi ($\times 10e4$) |
|---|---|---|---|---|---|---|---|---|
| | | P mg | Cu $\mu g$ | Fe $\mu g$ | Mn $\mu g$ | Zn $\mu g$ | | |
| control | 1.59 | 3.07 | 12.3 | 292 | 31.3 | 161 | 4.38 | 2.25 |
| rock P | 1.80 | 3.68 | 12.2 | 568 | 41.1 | 149 | 4.60 | 2.75 |
| P. bilaji | 2.95 | 5.32 | 19.3 | 359 | 32.3 | 232 | 6.10 | 8.75 |
| rock P + P. bilaji | 3.48 | 5.39 | 24.5 | 540 | 31.9 | 540 | 6.20 | 8.75 |
| Statistical Analysis | | | | | | | | |
| P. bilaji effect | ** | ** | * | ns | ns | ns | ** | ** |
| Rock P effect | ns | ns | ns | * | ns | ns | ns | ns |
| P. bilaji × RP | ns | ns | ns | ns | ns | * | ns | ns |

\* = significance at p < .05
\*\* = significance at p < .01
ns = non-significant effect These results of a greenhouse test show that addition of the *P. bilaji* fungus to the soil results in increased plant growth by increasing plant P uptake from rock phosphate and also increases the uptake of soil P. This appears to be a consequence of the fungus increasing the availability of soil and rock P as shown by the increase in Soil Available P as measured by extraction with sodium bicarbonate. The persistance of the inoculum is shown in that the incidence of P-solubilizing fungi in the inoculated treatments is greater than that found in the uninoculated pots. Pots inoculated with the fungus showed increased uptake of copper (Cu) and zinc (Zn) even though none of this material was added to the pots.

EXAMPLE 4

Source of Increased P supplied by Penicillium fungus Method

The P nutrition of wheat (*Triticum aestivum* L cv Neepawa) under greenhouse conditions was examined in a completely randomized block experiment utilizing eight replications of three main effects and their combinations: *P. bilaji*, Idaho rock phosphate and a mixed culture of vesicular-arbuscular mycorrhizal fungi (VAM). The preparation of the RP was the same as previously used. Where used, the RP was added at a rate equal to 72 Kg P/ha. The VAM inoculum consisted of 5 g of dried strawberry roots and adhering soil. The VAM inoculum in this form contained 24–28 VAM spores per gram of inoculum as determined by direct counts. The *P. bilaji* inoculum was raised for 3 days at 30° C. on moistened sterilized wheat chaff amended with 1% dextrose (w/w). The wheat chaff acted as a carrier for the hyphae growing on its surface and the spores produced. Five grams wet weight of chaff was used per pot where appropriate.

The test soil used (Ap, 0–15 cm, of a Cavendish loamy sand, Orthic Brown Chernozem) had a pH of 8.0 (1:1 water paste) contained 3.6% org. matter and contained 3 $\mu$g NaHCO$_3$ ext. P per gram of soil. Bulk soil was moistened and autoclaved to kill the native VAM and incubated in an uncovered condition for seven weeks prior to use to allow for re-equilibration of soil nutrients and microbial populations. The soil was uniformly labelled with P-32; 9 mg P as KH$_2$PO$_4$ was added to 230 kg soil six weeks prior to the planting of seeds. Weighed amounts of soil equivalent to 1.0 kg dry soil was placed into 15 cm dia. ceramic pots. The *P. bilaji* where used was placed in a hole bored in the center of each pot and covered with the soil from the hole. Rock phosphate, if used, was mixed with the soil from the center hole prior to replacing it in the pot. VAM inoculum was placed beneath each seed located between the edges of the pot and the center hole.

Six wheat seeds were planted per pot and later thinned to four plants per pot after emergence, at which time 50 $\mu$g N/g soil was added as NH$_4$NO$_3$. The plants were grown in a greenhouse under controlled conditions (16/8 day night, 20°/16° C.). Pots were weighed daily and water added to maintain the soil at field capacity. Plant tops were harvested at the early heading stage, oven-dried (70° C.) to a constant weight, weighed and ground to pass a 40 mesh seive. A 0.5 g subsample of ground plant material was wet digested and aliquots of the digest were colorimetrically analyzed for P content, and for P-32 content using liquid scintillation counting methods. The specific activities of plant P in the treatments were compared to determine the proportion of P in the plant coming from unlabelled sources. The percentage of P calculated as being derived from the soil P that was isotopically exchangeable with the added P-32 is calculated by:

$$\% \text{ P from labelled pool (\% Pdlp)} = \frac{\text{sp.act. of P (treat)}}{\text{sp.act. of P (cont)}} \times 100$$

The phosphorus derived from unlabelled sources was calculated by:

$$\% \text{ P from unlabelled pool} = 100 - \% \text{ Pdlp}$$

Results:

TABLE 5

| Treatment | Dry Matter g/pot | Total P mg/pot | % PdfL | % PdfUL |
|---|---|---|---|---|
| Control | 4.27 | 6.32 | 100 | 0 |
| P. bilaji | 5.75 | 7.99 | 82.3 | 17.7 |
| VAM | 4.36 | 6.67 | 96.6 | 3.4 |
| RP | 4.59 | 6.47 | 89.7 | 10.3 |
| RP + P. bilaji | 5.88 | 8.06 | 87.9 | 12.1 |
| RP + VAM | 4.98 | 6.87 | 91.2 | 8.8 |
| P. bilaji + VAM | 5.43 | 7.98 | 88.3 | 11.7 |
| Statistical Analysis | | | | |
| Rock P | ns | ns | * | * |
| VAM | ns | ns | ns | ns |
| P. bilaji | ** | ** | ** | ** |
| VAM + P. bilaji | * | ns | ns | ns |
| VAM + Rock P | ns | ns | ns | ns |
| P. bilaji + Rock P | ns | ns | ns | ns |

TABLE 5-continued

| Treatment | Dry Matter g/pot | Total P mg/pot | % PdfL | % PdfUL |
|---|---|---|---|---|
| VAM + RP + P. bilaji | ns | ns | ns | ns |

\* = significance at p < .05
\*\* = significance at p < .01
ns = non-significant effect A significant (p<.01) increase in dry matter production and P content of wheat was measured as a response to inoculation of soil with P.bilaji. When all treatments involving P.bilaji are averaged and compared to the averages of all the treatments lacking P.bilaji, Neepawa wheat exhibited an overall 25% increase in plant dry matter yield and this was matched by an overall 22% increase in total P uptake.

The addition of RP did not affect wheat dry matter production or P uptake. Comparison of the specific activites of the plant P showed a significant effect of P.bilaji and of the addition of RP on the source of P absorbed by the plants. The addition of RP to the soil resulted in P-32 isotopic dilution of the plant absorbed P which could be calculated to mean that the RP supplied roughly 10% of the plant P both with and without VAM inoculation. RP did not however increase P supply in the soil as a whole as indicated by a lack of increase in plant P uptake for plants receiving RP alone. VAM inoculation alone did not have an effect on the plant specific activity.

Inoculation of the soil with P.bilaji resulted in P-32 isotopic dilution, even in the absence of added RP. This indicates that the Penicillium fungus was able to cause the release of P from unlabelled sources, which in this case could only be from native soil P that was not isotopically exchangeable. This can be stated with confidence since plant P uptake was increased as well. When the fungus was added along with RP, no further isotopic dilution and only small increases in total P uptake were observed. This could mean that the fungus did not have a significant effect on solubilization of added RP, or, if isotopic exchange did occur between the RP and soil P, then the fungus could be acting to release the exchangeable portion of the P in rock phosphate, which would result in the re-release of the P-32. Double inoculation of pots with VAM and P.bilaji was not more effective than addition of P.bilaji alone, but was superior to the addition of VAM alone. The treatment with the highest dry matter production and total P uptake was the treatment including P.bilaji+RP. This indicates solubilization of rock phosphate since the total P uptake was increased above levels observed for treatments with P.bilaji.

EXAMPLE 5

Effectiveness of method used by Penicillium bilaji for solubilizing phosphorus

Method

Solution culture studies tested the interactions of the following treatments: P-solubilizing fungi, rock phosphate (RP) and nitrogen form. The fungal treatments used were: Penicillium bilaji (Chalabuda) and P. fuscum (Sopp) biorge sensu. as well as uninoculated controls. The Penicillium isolates were chosen from previous tests in which P.bilaji was found to be an effective P-solubilizer. Penicillium fuscum was previously found to be less effective and was used for comparison. From pure cultures of these isolates, maintained on Soil Extract agar slants, fresh inoculum was prepared by inoculating the individual isolates onto Potato Dextrose agar plates and incubating them at 30° C. for three days prior to use. Pieces of agar on which were growing hyphae supporting spores were cut from the growing colonies and added to the experimental units.

Idaho RP (10.3% P) was sieved and the fine material was dry autoclaved. Rock phosphorus treatments used included: 0.1 g per 100 ml solution media, 0.2 g per 100 ml media and unamended controls. The solution media used differed in the chemical form of N supplied in that media A contained equimolar amounts of $NH_4$ and $NO_3$ while Media B contain only $NO_3$. One hundred ml of one of the solutions was measured into 250 ml screw top polypropylene centrifuge bottles and sterilized by autoclaving before addition of the RP and/or Penicillium isolates. All transfers of fungal inocula, RP and subsequent sampling of culture solutions were carried out aseptically in a laminar flow cabinet.

Incubation of the 36 experimental units (3 media×3 fungi×3 RP×4 reps) was conducted on a bench-top rotary shaker (200 rpm, 24° C.). To ensure adequate aeration of the solution cultures, the screw caps of the bottles were loosened to allow gas exchange but minimize air-borne contamination. Once daily, for 12 days, a 5 ml subsample of growth medium was withdrawn from each bottle. The subsample was centrifuged (10K rpm for 5 min.) and the supernatant decanted and filtered. The pH of the supernatant was measured using a pH meter and the P in solution was determined using the colorimetric stannous chloride-molybdate blue method (Olsen et al, 1954). The P solubilized by the fungi was compared to the P dissolved by the addition of HCl in the same solution culture. Increasing amounts of 0.1 N HCl were added to bottles of solution media containing 0.2 g RP. The solution pH was measured at the beginning of the experiment and again after 240 hours. The P in solution was measured after 240 hours by colorimetric methods. The P in solution and the corresponding solution pH after 240 hours incubation were used for comparison to the maximum P in solution and minimum pH of the fungal cultures, taking into consideration the volume of solution culture remaining on the day of maximum P concentration.

Results:

Minimum solution pH and Maximum P in solution caused by 2 Penicillium isolates and 0.1N HCl.

TABLE 6

| Pen. isolate | Min. Soln. pH | Max. Soln P. Conc. µg/ml | Max. P in Soln mg | P dissolved by 0.1N HCl mg | P(fung) P(acid) |
|---|---|---|---|---|---|
| Media A (with $NH_4$) | | | | | |
| P. bilaji | 3.7 | 258 | 14.2 | 4.5 | 3.2 |
| P. fuscum | 4.1 | 203 | 10.2 | 1.6 | 6.4 |
| Media B (no $NH_4$) | | | | | |
| P. bilaji | 4.0 | 46 | 2.5 | 2.1 | 1.2 |
| P. fuscum | 6.2 | 7 | 0.4 | .06 | 6.7 |

The amount of P solubilized by P.fuscum was directly related to the drop in media pH produced, showing that this isolate relied primarily on a mechanism requiring $NH_4$ to release P. The P solubilized by P.bilaji, however, did not show this relationship. Obviously the acidity generated by a second mechanism, ie that not requiring $NH_4$, was not as effective at solubilizing RP since the pH of media A and B were not significantly different but the levels of P released were.

The P solubilized by the fungi in media A was greater than that released by acid dissolution of RP at equivalent solution pH's, even after 240 hours exposure to the acid. This indicates that both fungi, in the presence of $NH_4$ were not strictly relying on the production of acid to dissolve P, but were relying on another mechanism, possibly excretion of organic acid metabolites, to cause P release, and that this system was more effective at solubilizing P than strict acid dissolution. In media B, the P released by *P.bilaji* was equivalent to that released by exposure to HCl, giving evidence that a mechanism not requiring $NH_4$ was possibly a strict acidifying effect. The P released by *P.fuscum*, while exceptionally low, was still greater than that released by HCl, indicating that the same mechanism was being utilized by this isolate in the presence and absence of ammonium ions.

*P.bilaji* appears to employ two mechanisms in lowering the media pH, one mechanism relying on the presence of $NH_4$, while the second does not require ammonium. *P.fuscum* appears to employ only an ammonium requiring system which may be different from that used by *P.bilaji*. The mechanism requiring $NH_4$ is more effective than straight acid dissolution of rock P.

EXAMPLE 6

An experiment was conducted on a Black Chernozemic soil located at the University of Alberta, Edmonton, Alberta. The soil had a pH of 6.0 (0.01m $CaCl_2$) and low levels of available phosphorus. Canola (cv Westar) was used as a test crop. Each plot consisted of four treatment rows 7.62 m long separated from the other treatments by a guard (i.e. untreated) row. Rows were spaced 17.8 cm apart.

Florida rock phosphate and commercial monoammonium phosphate (MAP) were used as phosphorus sources. The rock phosphate was granulated by heating with urea (140° C) for eight hours, then cooling the mixture, and sieving out granules with sizes between 1 and 2.5 mm diameter. The final product contained 10% nitrogen and 28% $P_2O_5$ *Penicillium bilaji* inocula was prepared by growing the fungus on moistened sterile bran at room temperature (20° C) for one week. The colonized bran was air dried and used directly for application as seed row inoculum. The air-dried bran contained $9 \times 10^{10}$ colony forming units per gram.

Four fertilizer (control, rock phosphate, ½ MAP, MAP) and two fungal treatments (control, *P. bilaji*) were used in a factorial design with five replications. The full MAP and rock phosphorus treatment received 12.2 kgP/ha equivalent, while the ½ MAP treatment received 6.1 kgP/ha, added in the seed row below the seeds. Treatments receiving bran applied *P.bilaji* received 2.0 g bran per meter of row added in the seed row. Nitrogen as ammonium nitrate was added at a rate equal to 78 kgN/ha at seeding using broadcast methods. All fertilizers, inocula and seeds were added through a mechanical seeder with attachments for adding additional materials. 6.0 meters of row were mechanically harvested for determination of grain weights from each plot at maturity.

TABLE 7

| Analysis of Canola data, Univ. of Alberta | |
|---|---|
| | Grain Yield (g/6 m) |
| No P | |
| − P. bilaji | 508 |
| + P. bilaji | 558 |
| Rock P | |
| − P. bilaji | 484 |
| + P. bilaji | 614 |
| ½ MAP | |
| − P. bilaji | 443 |
| + P. bilaji | 554 |
| MAP | |
| − P. bilaji | 531 |
| + P. bilaji | 550 |
| Main Effects | |
| Fertilizer form | |
| control | 532a |
| rock P | 556a |
| ½ MAP | 499a |
| MAP | 540a |
| P. bilaji | |
| − P. bilaji | 492a |
| + P. bilaji | 570 b |
| Analysis of Variance | |
| Fert | ns |
| P. bilaji | .01 |
| F*P | ns |

The results show that the addition of *P. bilaji* to canola crops was able to increase the grain yields by 10% in the absence of added phosphorus and to increase grain yields by 27% in the case of added rock phosphate. The Florida phosphate was unavailable for plant uptake in the absence of the organism. Plant responses to rock phosphate in conjunction with *P. bilaji* were greater than those obtained from the addition of MAP at an equal level of phosphorus addition. Overall, the main effect of *P. bilaji* addition was to increase grain yields by 16% (*P. bilaji*/−*P. bilaji* main effect).

EXAMPLE 7

A greenhouse formulation experiment was conducted in the summer and fall of 1987. A 1:1 mixture of beach sand and soil from Purple Springs Alberta was used. The resulting mixture (pH 7.2 (1:1 $CaCl_2$) was inoculated with VA mycorrhizal fungi and 1.2 Kg were added to each of 200 clay pots. The soil was watered 2 days before seeding. The soil moisture was maintained at field capacity by daily watering.

Florida rock phosphate was used in this experiment. The rock phosphate (10.2% P) was added at 20 mg P/kg soil. Monoammonium Phosphate (11 51 0) was added at 20 mg P/kg soil to one set of pots as a control treatment. The phosphorus was added to the soil in a layer 1 cm below the seed. Nitrogen as $NH_4Cl$ was added to the appropriate pots so that the nitrogen in each pot would be equivalent to that in pots with MAP. Micronutrients were added at planting and every two weeks thereafter. Additional nitrogen was added as $NH_4NO_3$ (50 mg N/kg soil) 1 and 4 weeks after planting and as $(NH_4)_2SO_4$ (50 mg N/kg soil) 6 weeks after planting.

The *P. bilaji* inoculum was added either as a seed treatment or as a bran based soil applied application. Two seed treatment formulations were used. The first consisted of spores mixed in a carrier of 50:50 soluble starch and cellulose (ST-Cell). The base material contained $5.6 \times 10^9$ colony-forming units (cfu) *P. bilaji*/g material. Serial dilutions of this material were prepared by mixing the base *P. bilaji* containing substrate with autoclaved starch cellulose. This material was then used to coat wheat seed (cv. Neepawa). 5.0 g of material was mixed with 14 ml of H₂O and 5.0 ml of the resulting suspension was added to 10 g of wheat seed. The seeds were allowed to dry overnight at room temperature. Four *P. bilaji* concentrations were used. The first SC1 used the base material and resulted in a *P. bilaji* concentration of $8.4 \times 10^5$ cfu/seed. The remaining which were serial dilutions of the base material contained $1.13 \times 10^5$ (SC2); $1.46 \times 10^4$ (SC3); and $5.0 \times 10^3$ (SC4) cfu *P. bilaji*/seed. Control seed was coated with the starch cellulose carrier alone (no *P. bilaji*).

The second seed treatment used *P. bilaji* inoculum prepared by growing the fungus on moistened bran. The bran was inoculated with spores of the fungus and allowed to grow for 1 week at room temperature. This material was dried and sieved (2 mm). The sieved material which contained $3.5 \times 10^9$ cfu *P. bilaji*/g dry bran was mixed with wheat seed which had been coated with Gum Arabic sticker. This coated seed was then sieved through a 2 mm sieve to remove excess bran. Serial dilutions of the bran were prepared by mixing bran inoculated with *P. bilaji* with uninoculated bran. Four *P. bilaji* concentrations were used. The first SB1 used only inoculated bran and had a *P. bilaji* concentration of $1.74 \times 10^6$ cfu *P. bilaji*/seed. The remaining treatments, SB2, SB3, and SB4 had concentrations of $2.2 \times 10^5$, $7.57 \times 10^4$, and $2.67 \times 10^3$ cfu *P. bilaji*/seed, respectively. Control seed was not treated.

The soil applied bran used the same *P. bilaji* containing bran used in the second seed treatment. Three rates of this material were used. LB1, LB2, and LB3 were applied at 1.0, 0.1, and 0.01 g/pot, respectively. The bran was applied to the soil in a layer 1 cm below the seed.

Ten seeds were planted in each pot and were thinned to 5 seeds/pot after emergence was completed. The pots were arranged in a randomized block design with 5 replications. There were 27 treatments (Table 8). The plants were harvested 10 weeks after planting. Total oven dry weight and phosphorus content were determined. The results are shown in Table 8 and Table 9 below.

TABLE 8

| Treatments Formulation Experiment | | |
|---|---|---|
| 1. NO *P. bilaji*/NO P | 2. NO *P. bilaji*/RP | 3. NO *P. bilaji*/MAPF |
| 4. SC0/NO P | 5. SC0/RP | |
| 6. SC1/NO P | 7. SC1/RP | |
| 8. SC2/NO P | 9. SC2/RP | |
| 10. SC3/NO P | 11. SC3/RP | |
| 12. SC4/NO P | 13. SC4/RP | |
| 14. SB1/NO P | 15. SB1/RP | |
| 16. SB2/NO P | 17. SB2/RP | |
| 18. SB3/NO P | 19. SB3/RP | |
| 20. SB4/NO P | 21. SB4/RP | |
| 22. LB1/NO P | 23. LB1/RP | |
| 24. LB2/NO P | 25. LB2/RP | |
| 26. LB3/NO P | 27. LB3/RP | |

TABLE 9

| Analysis of Inoculation Formulation Experiment | | | | | |
|---|---|---|---|---|---|
| | | Dry Matter (g/pot) | | Total P (mg/pot) | |
| *P. bilaji* Form | inoc Rate | No P | Rock P (20 kg) | No P | Rock P (20 kg) |
| St-Cell | $10^3$ | 2.20 | 2.01 | 4.11 | 4.29 |
| | $10^4$ | 1.45 | 2.72 | 2.60 | 5.04 |
| | $10^5$ | 1.72 | 2.01 | 2.66 | 3.88 |
| | $10^6$ | 1.94 | 2.08 | 3.10 | 4.24 |
| Bran-seed | $10^3$ | 2.38 | 1.74 | 4.15 | 3.04 |
| | $10^4$ | 2.10 | 1.84 | 3.35 | 3.15 |
| | $10^5$ | 1.73 | 1.71 | 2.67 | 3.19 |
| | $10^6$ | 1.40 | 1.72 | 2.65 | 2.81 |
| Bran-row | $10^4$ | 2.40 | 2.24 | 4.29 | 4.09 |
| | $10^5$ | 2.54 | 2.47 | 4.06 | 4.10 |
| | $10^6$ | 3.13 | 3.46 | 5.50 | 5.72 |
| Control | — | 1.77 | 1.78 | 2.73 | 3.11 |
| St-Cell | — | 1.91 | 1.24 | 2.72 | 1.73 |
| MAP (20 kgP) | | 3.74 | 3.74 | 8.13 | 8.13 |
| LSD (.05) | | .75 | .78 | 1.69 | 1.85 |
| Analysis of Var. | | | | | |
| form | | .01 | .01 | .01 | .01 |
| rate | | ns | ns | .05 | ns |
| rate*form | | ns | .01 | ns | .05 |
| Main Effect | | | | | |
| St-Cell | | 1.80 | 2.21 | 3.18 | 4.36 |
| Bran-seed | | 1.90 | 1.75 | 3.21 | 3.05 |
| Bran-row | | 2.69 | 2.72 | 4.61 | 4.64 |
| MAP (20) | | 3.74 | 3.74 | 8.13 | 8.13 |
| Control | | 1.77 | 1.78 | 2.73 | 3.12 |
| LSD (.05) | | .56 | .59 | 1.26 | 1.38 |

A significant difference was observed between the three inoculum forms with respect to plant growth and phosphorus uptake response. The most effective treatment was the bran inoculum added in the seed row, however the starch cellulose inoculum was also effective in the case of pots receiving additional rock phosphate.

With respect to inoculum level, the results show that the rate of inoculum addition did not significantly affect the response of the crop. In the case of the starch cellulose inoculum, the most effective rate was $10^4$ cfu/seed which gave a growth response to rock phosphate equal to 59% of that resulting from the addition of MAP (SC-cont/MAP-cont) and a phosphorus uptake response equal to 52% of that from MAP. With the bran inoculum added in the seed row, the most effective rate of addition was $10^6$ cfu/seed which gave a plant growth response equal to 86% of that produced by MAP, and a phosphorus uptake response equal to 52% of that from MAP. By comparison of the control pots with and without rock phosphate, it is evident that the rock phosphate in the absence of *P. bilaji* was not available for plant uptake.

The results for both pots receiving rock phosphate and those without added rock phosphate clearly show the benefits from the addition of this organism. *Penicillium bilaji*, in this experiment was shown to increase plant growth responses to the addition of Florida rock phosphate, and to increase plant growth in the absence of added phosphorus.

EXAMPLE 8

A greenhouse formulation experiment was conducted as follows. A 1:1 mixture of beach sand and soil from Purple Springs, Alberta was used. The resulting mixture (pH 7.2 (1:1 CaCl₂)) was inoculated with VA mycorrhizal fungi and 1.2 Kg were added to each of 200 clay pots. The soil was watered 2 days before seeding. The soil moisture was maintained at field capacity by daily watering.

Mono-ammonium Phosphate (11-51-0) was added at either 20 mg P/kg soil (full rate - MAPF) or 10 mg P/kg soil (half rate - MAPH). Control pots not receiving P fertilizer were also included. The phosphorous was added to the soil in a layer 1 cm below the seed. Nitrogen as $NH_4Cl$ was added to the appropriate pots (all but those containing MAPF) so that the nitrogen in each pot would be equivalent to that in pots with MAPF. Micronutrients were added at $NH_4NO_3$ (50 mg N/kg soil) 1 and 4 weeks after planting and as $(NH_4)_2SO_4$ (50 mg N/kg soil) 6 weeks after planting.

The *P. bilaji* was added either as a seed treatment or as a bran based soil applied application. Two seed treatment formulations were used. The first consisted of spores mixed in a carrier of 50:50 soluble starch and cellulose (ST-Cell). The base material contained $5.6 \times 10^9$ colony forming units (cfu) *P. bilaji*/g material. Serial dilutions of this material were prepared by mixing the base *P. bilaji* containing substrate with autoclaved starch cellulose. This material was then used to coat wheat seed (cv. Neepawa). 5.0 g of material was mixed with 14 ml of $H_2O$ and 5.0 ml of the resulting suspension was added to 10 g of wheat seed. The seeds were allowed to dry overnight at room temperature. Four *P. bilaji* concentrations were used. The first (SC1) used the base material and resulted in a *P. bilaji* concentration of $8.4 \times 10^5$ cfu/seed. The remaining $1.46 \times 10^4$ (SC3); and $5.0 \times 10^3$ (SC4) cfu *P. bilaji*/seed. Control seed was coated with the starch cellulose carrier alone (no *P. bilaji*).

The second seed treatment used *P. bilaji* inoculum prepared by growing the fungus on moistened bran. The bran was inoculated with spores of the fungus and allowed to grow for 1 week at room temperature. This material was dried and sieved (2 mm). The sieved material which contained $3.5 \times 10^9$ cfu *P. bilaji*/g dry bran was mixed with wheat seed which had been coated with Gum Arabic sticker. This coated seed was then sieved through a 2 mm sieve to remove excess bran. Serial dilutions of the bran were prepared by mixing bran inoculated with *P. bilaji* with uninoculated bran. Four *P. bilaji* concentrations were used. The first (SB1) used only inoculated bran and had a *P. bilaji* concentration of $1.74 \times 10^6$ cfu *P. bilaji*/ seed. The remaining treatments, SB2, SB3, and SB4 had concentrations of $2.2 \times 10^5$, $7.57 \times 10^4$, and $2.67 \times 10^3$ cfu *P. bilaji*/seed, respectively. Control seed was not treated.

The soil applied bran used the same *P. bilaji* containing bran used in the second seed treatment. Three rates of this material were used. LB1, LB2, and LB3 were applied at 1.0, 0.1, and 0.01 g/pot, respectively. The bran was applied to the soil in a layer 1 cm below the seed.

Ten seeds were planted in each pot and were thinned to 5 seeds/pot after emergence was completed. The pots were arranged in a randomized block design with 5 replications. There were 27 treatments (Table 10a). The plants were harvest 10 weeks after planting. Total oven dry weight and p content were determined. The results are shown in Table 10b.

TABLE 10a

Treatments Formulation Experiment

| 1. NO *P. bilaji*/NO P | 2. NO *P. bilaji*/NAOG | 3. NO *P. bilaji*/MAPF |
|---|---|---|
| 4. SC0/NO P | 5. SC0/MAPH | |
| 6. SC1/NO P | 7. SC1/MAPH | |
| 8. SC2/NO P | 9. SC2/MAPH | |
| 10. SC2/NO P | 11. SC3/MAPH | |
| 12. SC4/NO P | 13. SC4/MAPH | |
| 14. SB1/NO P | 15. SB1/MAPH | |

TABLE 10a-continued

Treatments Formulation Experiment

| 16. SB2/NO P | 17. SB2/MAPH |
| 18. SB3/NO P | 19. SB3/MAPH |
| 20. SB4/NO P | 21. SB4/MAPH |
| 22. LB1/NO P | 23. LB1/MAPH |
| 24. LB2/NO P | 25. LB2/MAPH |
| 26. LB3/NO P | 27. LB3/MAPH |

TABLE 10b

Analysis of Inoculation Formulation Experiment

| *P. bilaji* Form | inoc Rate | Dry Matter (g/pot) | | Total P (mg/pot) | |
|---|---|---|---|---|---|
| | | No P | MAP (10 kg) | No P | MAP (10 kg) |
| St-Cell | $10^3$ | 2.20 | 3.33 | 4.11 | 5.92 |
| | $10^4$ | 1.45 | 3.30 | 2.60 | 5.63 |
| | $10^5$ | 1.72 | 2.50 | 2.66 | 4.63 |
| | $10^6$ | 1.94 | 3.12 | 3.10 | 5.40 |
| Bran-seed | $10^3$ | 2.38 | 3.33 | 4.15 | 5.42 |
| | $10^4$ | 2.10 | 2.80 | 3.35 | 5.56 |
| | $10^5$ | 1.73 | 3.09 | 2.67 | 5.05 |
| | $10^6$ | 1.40 | 3.05 | 2.65 | 5.10 |
| Bran-row | $10^4$ | 2.40 | 2.98 | 4.29 | 6.50 |
| | $10^5$ | 2.54 | 3.24 | 4.06 | 6.70 |
| | $10^6$ | 3.13 | 4.52 | 5.50 | 9.00 |
| Control | — | 1.77 | 2.93 | 2.73 | 5.04 |
| St-Cell | — | 1.91 | 2.97 | 2.72 | 4.85 |
| MAP (20 kgP) | | 3.74 | 3.74 | 8.13 | 8.13 |
| LSD (.05) | | .75 | 1.04 | 1.69 | 2.49 |
| Analysis of Var. | | | | | |
| form | | .01 | ns | .01 | .01 |
| rate | | ns | ns | .05 | ns |
| rate*form | | ns | ns | ns | ns |
| Main Effect | | | | | |
| St Cell | | 1.80 | 3.06 | 3.18 | 5.40 |
| Bran-seed | | 1.90 | 3.07 | 3.21 | 5.28 |
| Bran-row | | 2.69 | 3.58 | 4.61 | 7.40 |
| MAP (20) | | 3.74 | 3.74 | 8.13 | 8.13 |
| Control | | 1.77 | 2.93 | 2.73 | 5.04 |
| LSD (.05) | | .56 | .77 | 1.26 | 1.86 |

A significant difference was observed between the three inoculum forms with respect to plant growth response in the absence of added P and in the P uptake response to added MAP. The most effective treatment was the bran inoculum added in the seed row, however the starch cellulose inoculum was also effective in the case of pots receiving MAP.

With respect to inoculum level, the results show that the rate of inoculum addition did not significantly affect the response of the crop. In the case of the starch cellulose inoculum, the most effective rate was $10^3$ cfu/seed which gave a growth response to ½ the MAP rate equal to 23% of that resulting from the addition of the full rate of MAP (SC-cont/MAP-cont) and a P uptake response equal to 33% of that from MAP. With the bran inoculum added in the seed row, the most effective rate of addition was $10^6$ cfu/seed which gave a plant growth response the ½ the MAP rate equal to 196% of that produced by the full rate of MAP, and a P uptake response equal to 128% of that from the full rate of MAP. By comparison of the control pots with and without the addition of the ½ rate of MAP, it is evident that the soil was P deficient, and responded to the addition of AMP, and also that the ½ rate of MAP in the absence of *P. bilaji* was not as effective as the full rate of MAP.

The results for both plots receiving the ½ rate of MAP and those without added P clearly show the benefits from the addition of this organism. *Penicillium bilaji*, in this experiment was shown to increase plant growth responses to the addition of MAP, and to increase plant growth in the absence of added P.

EXAMPLE 9

An experiment was conducted on a Brown Chernozemic soil located on the Vauxhall substation of the Lethbridge Research Station. The soil had a pH of 7.6 (0.01'M $CaCl_2$) and low levels of available P. Corn (*Zea mays* cv Dward 39119YP) and spring wheat (*Triticum aestivum* cv Fielder) were used as test crops. Each plot consisted of four treatment rows 6.1m long separated from the other treatments by a guard (i.e. untreated) row. Wheat rows were spaced 17.8 cm apart while the corn rows were separated by 35.6 cm).

Florida rock phosphate and commercial monoammonium phosphate (MAP) were used as P sources. The rock phosphate was granulated by heating with urea (140° C.) for eight hours, then cooling the mixture, and seiving out granules with sizes between 1 and 2.5 mm diameter. The final product contained 10% N and 28% $P_2O_5$. *Penicillium bilaji* inoculum was prepared by growing the fungus on moistened sterile bran at room temperature (20° C.) for one week. The colonized bran was air dried and either used directly for application as seed row inoculum or added with the seeds along with gum arabic sticker and shaken to poduce seed coat applied material. The air-dried bran contained $9 \times 10^{10}$ colony forming units per gram. Seed applied *P. bilaji* was able to deliver $1.5 \times 10^6$ cfu per wheat seed and $1.1 \times 10^6$ per corn seed.

Three fertilizers (control, rock phosphate, MAP) and three fungal treatments (control, seed applied *P. bilaji*, bran applied *P. bilaji*) were used for each crop in a factorial design with five replications. Wheat plots, where applicable received 12.2 kg P.ha equivalent, as either rock phosphate or MAP, added in the seed row below the seeds. Corn plots received 20.0 kg P.ha equivalent. Treatments receiving bran applied *P. bilaji* received 0.9 g bran per meter of row added in the seed row. Nitrogen as ammonium nitrate was added to each crop at seeding using broadcast methods. Wheat plots received 78.4 kg N/ha equivalent while corn plate received 112 kg N/ha. Additional N as urea was added in each seed row at a rate to equal the amount of N added with the MAP for each crop. All fertilizers, inocula and seeds were added through a mechanical seeder with attachments for adding additional materials. Plots were hand weeded. All plots received supplemental irrigation water as necessary to maintain soil moisture tension below −450 KPa as measured with tensiometers located within the plots. Ten plants were harvested at maturity. The results are shown in Tables 11a and 11b.

TABLE 11a

Effect of *Penicillium bilaji* on wheat growth

| | TOTAL DRY MATTER | GRAIN YIELD |
|---|---|---|
| NO P | | |
| No P. bilaji | 482 b | 226 b |
| Seed P. bilaji | 551 ab | 249 ab |
| Bran P. bilaji | 535 b | 254 ab |
| ROCK P | | |
| No P. bilaji | 511 b | 229 ab |
| Seed P. bilaji | 510 b | 223 b |
| Bran P. bilaji | 546 ab | 249 ab |
| MAP | | |
| No P. bilaji | 515 b | 242 ab |
| Seed P. bilaji | 533 ab | 248 ab |
| Bran P. bilaji | 617 a | 277 a |

TABLE 11a-continued

Effect of *Penicillium bilaji* on wheat growth

| | TOTAL DRY MATTER | GRAIN YIELD |
|---|---|---|
| Main Effects | | |
| Fertilizer form | | |
| No P | 523 a | 243 a |
| Rock P | 522 a | 234 a |
| MAP | 555 a | 256 a |
| P. bilaji | | |
| − P. bilaji | 503 a | 232 a |
| + P. bilaji seed | 531 ab | 240 ab |
| + P. bilaji bran | 566 b | 260 b | values in each column followed by the same letter are not sig. diff. as determined by LSD analysis on log transformed data.

Analysis of Variance

| Fert | ns | ns |
| P. bilaji | .05 | .10 |
| FxP | ns | ns |

TABLE 11b

Effect of *P. bilaji* on Corn Growth

| | TOTAL DRY MATTER | GRAIN YIELD |
|---|---|---|
| NO P | | |
| No P. bilaji | 1925 bc | 968 bc |
| Seed P. bilaji | 2227 abc | 1088 ab |
| Bran P. bilaji | 2295 ab | 1156 ab |
| ROCK P | | |
| No P. bilaji | 1893 c | 843 c |
| Seed P. bilaji | 1950 bc | 954 bc |
| Bran P. bilaji | 2029 abc | 1055 ab |
| MAP | | |
| No P. bilaji | 2163 abc | 1146 ab |
| Seed P. bilaji | 2246 abc | 1126 a |
| Bran P. bilaji | 2357 a | 1196 a |
| Main Effects | | |
| Fertilizer form | | |
| No P | 2149 ab | 1071 a |
| Rock P | 1957 b | 951 b |
| MAP | 2255 a | 1156 a |
| P. bilaji | | |
| − P. bilaji | 1994 a | 986 a |
| + P. bilaji seed | 2141 ab | 1056 ab |
| + P. bilaji bran | 2227 b | 1136 b | values in each column followed by the same letter are not sig. diff. as determined by LSD analysis on log transformed data.

Analysis of Variance

| Fert | .05 | .01 |
| P. bilaji | .10 | .05 |
| FxP | ns | ns |

*P. bilaji* inoculum added as a bran based material in the seed row was much more effective than the seed applied inoculum for both crops. The seed and row applied inocula were compared in the previous Example, and the seed applied form was shown there to be inferior. However, in that Example, a different form of seed applied inoculum, using starch-cellulose instead of bran, was shown to be better than the seed applied inoculum used in this experiment. Consequently, it is concluded that it is the form, not the method, of applying the inoculum to seeds that results in poor performance.

The results for the wheat experiment show that *P. bilaji*, applied in the seed row, was able to increase plant yields by 20%, and grain yields by 14.5% over uninoculated wheat plants in plots receiving MAP. *P. bilaji* was also able to increase plant and grain yields by 11% and 12% resp. over uninoculated plants in unfertilized plots. Since the increase in plant growth due to *P. bilaji* for plots receiving MAP was greater than that observed for plots without MAP, we may conclude that the fungus is increasing the effectiveness of MAP as well as solubilizing soil inorganic phosphate.

Similarly, in the corn experiment, *P. bilaji*, applied in the seed row, was able to increase plant yields by 9%, and grain yields by 4% over uninoculated wheat plants in plots receiving MAP. *P. bilaji* was also able to increase plant and grain yields by 19% over uninoculated plants in unfertilized plots. The percentage increases for corn plots receiving MAP are smaller than that observed for the wheat experiment because of the greater yields of the control plots in the corn experiment. In the corn experiment, the increased yields in the MAP fertilized plots were smaller than those observed in the unfertilized plots. This may be due to over-fertilization of the corn plots with MAP, such that additional increases due to increased effectiveness are unlikely.

EXAMPLE 10

Experiments were conducted at ten sites in Alberta, Manitoba and Saskatchewan covering Brown, D. Brown and Black Chernozemic soils. The soils ranged in pH from 5.8 to 7.3 (0.01M $CaCl_2$) and low levels of available P. Spring wheat and barley were used as test crops. Each plot consisted of four treatment rows 7.62m long separated from the other treatments by a guard (i.e. untreated) row. Wheat and barley rows were spaced 17.8 cm apart.

Commercial mono-ammonium phosphate (MAP) was used as a P source. *Penicillium bilaji* inoculum was prepared by growing the fungus on moistened sterile bran at room temperature (20° C.) for one week. The colonized bran was air dried and used directly for application as seed row inoculum at the Gibbons site. The air-dried bran contained $9 \times 10^{10}$ colony forming units per gram. At the other sites, the inoculum was added to the seeds along with gum arabic (10% in $H_2O$) to provide between $6.3 \times 10^5$ and $6.1 \times 10^6$ per seed.

Five rates of fertilizer (0, 11, 22, 33, 44 kg $P_2O_5$/ha) and two fungal treatments (control, *P. bilaji*) were used for each experiment in a factorial design with five replications. The MAP was added in the seed row below the seeds. Treatments receiving bran applied *P. bilaji* received 2.0 g bran per meter of row added in the seed row. Nitrogen as ammonium nitrate was added to each crop at seeding using broadcast methods. Wheat and barley pots received 78.4 kg N/ha equivalent. All fertilizers, inocula and seeds were added through a mechanical seeder with attachments for adding additional materials.

At maturity, the central portions of the center four rows of each plot were mechanically harvested for grain yield (12.3 m row harvested total).

TABLE 12

| | | Analysis of MAP rate trials Grain yield (g/12.3 m) 5 reps | | | | | | | | |
|---|---|---|---|---|---|---|---|---|---|---|
| | | Gibbons | | U of A | Elstow | Rosthern | | Plum Coolee | | Oak Bluff | |
| Rate | *P. bilaji* | wheat | barley | wheat | wheat | wheat | barley | wheat | barley | wheat | barley |
| 0 | − | 714 | 1001 | 575 | 474 | 2161 | 1931 | 252 | 505 | 1242 | 1456 |
| 0 | + | 736 | 1131 | 557 | 478 | 2048 | 2090 | 302 | 617 | 1201 | 1489 |
| 10 | − | 784 | 1081 | 588 | 474 | 2200 | 2169 | 321 | 554 | 1306 | 1645 |
| 10 | + | 716 | 1071 | 529 | 523 | 2347 | 2127 | 320 | 574 | 1142 | 1682 |
| 20 | − | 804 | 947 | 636 | 557 | 2468 | 2028 | 345 | 603 | 1285 | 1827 |
| 20 | + | 741 | 945 | 599 | 504 | 2576 | 2081 | 351 | 604 | 1157 | 1687 |
| 30 | − | 743 | 1149 | 609 | 528 | 2542 | 2227 | 308 | 554 | 1224 | 1847 |
| 30 | + | 729 | 851 | 629 | 500 | 2635 | 2086 | 341 | 626 | 1137 | 1715 |
| 40 | − | 743 | 1016 | 610 | 465 | 2460 | 1995 | 304 | 627 | 1279 | 1757 |
| 40 | + | 768 | 1125 | 590 | 511 | 2567 | 2286 | 328 | 643 | 1142 | 1779 |
| LSD (p < .05) | | 130 | 231 | 101 | 90 | 286 | 436 | 53 | 116 | 107 | 104 |
| Main Effects | | | | | | | | | | | |
| − *P. bilaji* | | 758a | 1039a | 603a | 500a | 2362a | 2070a | 306a | 564a | 1267a | 1706a |
| + *P. bilaji* | | 739a | 1028a | 581a | 503a | 2429b | 2133a | 329a | 616b | 1155b | 1670a |
| Analysis of Variance | | | | | | | | | | | |
| MAP rate | | ns | ns | ns | ns | .01 | ns | .01 | ns | ns | .01 |
| *P. bilaji* | | ns | ns | ns | ns | .05 | .10 | .10 | .05 | .01 | ns |
| R*P | | ns | .05 | ns | .05 | ns | ns | ns | ns | ns | .05 |

The results indicate that the addition of *P. bilaji* to wheat and barley crops significantly (p<0.05) or nearly significantly (p<0.10) increased grain yields in 4 out of the ten experiments conducted. Of the remaining six experiments, only one site responded to the addition of MAP, so increased responses to *P. bilaji* should not be expected. Nonetheless, two of the responsive experiments were on sites where the crop did not respond to the addition of MAP, showing that MAP by itself is not effective in all prairie soils. This confirms previous data by other workers for Alberta soils. Bearing this in mind, *P. bilaji* inoculation resulted in increased grain yields in two of the three experiments which responded to MAP and also caused increases in two other experiments which did not respond to MAP.

Overall, the addition of *P. bilaji* at the four responsive sites resulted in an average increase in grain yields of 5.7% over uninoculated plots. One experiment, Oak Bluff wheat, resulted in a significant decrease in grain yield in response to *P. bilaji* addition, however, the reason for this is unexplained.

The increased response of crops to MAP plus *P. bilaji* is most likely due to increased P availability. In the two sites which did not respond to MAP, but did respond to *P. bilaji*, it is likely that the fungus was able to counteract the action of the soil in reducing MAP effectiveness, in essence, making the fertilizer work the way it is supposed to. The organism probably also solubilized soil inorganic P forms which contribute to plant P nutrition.

EXAMPLE 11

Experiments were conducted at Elstow, Saskatchewan. The soil had a pH of 5.8 (0.01M $CaCl_2$) and low levels of available P. Barley was used as test crop. Each plot consisted of four treatment rows 7.62 m long separated from the other treatments by a guard (i.e. untreated) row. Barley rows were spaced 17.8 cm apart.

Commercial mono-ammonium phosphate (MAP) was used as a P source. *Penicillium bilaji* inoculum was prepared by growing the fungus on moistened sterile bran at room temperature (20° C.) for one week. The colonized bran was air dried and used directly for application as seed row inoculum at the Gibbons site. The air-dried bran contained $9 \times 10^{10}$ colony forming units per gram. At the other sites, the inoculum was added to the seeds along with gum arabic (10% in $H_2O$) to provide between $6.3 \times 10^5$ and $6.1 \times 10^6$ per seed.

Five rates of fertilizer (0, 11, 22, 33, 44, kg $P_2O_5$/ha) and two fungal treatments (control, P.bilaji) were used for each experiment in a factorial design with five replications. The MAP was added in the seed row below the seeds. Treatments receiving bran applied P.bilaji received 2.0 g bran per meter of row added in the seed row. Nitrogen as ammonium nitrate was added to each crop at seeding using broadcast methods. Barley plots received 78.4 kg N/ha equivalent. All fertilizers, inocula and seeds were added through a mechanical seeder with attachments for adding additional materials.

At maturity, one meter of the center two rows of each plot were hand harvested for determination of total dry matter production.

TABLE 13

| | Analysis of MAP trials - Elstow | |
|---|---|---|
| Rate | P. bilaji | Plant yield (g/2 m) |
| 0 | — | 53.2 |
| 0 | + | 102.0 |
| 10 | — | 64.0 |
| 10 | + | 126.9 |
| 20 | — | 65.5 |
| 20 | + | 97.2 |
| 30 | — | 65.7 |
| 30 | + | 86.3 |
| 40 | — | 44.4 |
| 40 | + | 95.1 |
| Main Effects | | |
| — P. bilaji | | 58.6a |
| + P. bilaji | | 101.5 b |
| Analysis of Variance | | |
| MAP rate | | ns |
| P. bilaji | | .01 |
| R*P | | ns |

The results clearly show increased yields of barley, even though the crop did not respond to MAP addition. The ineffectiveness of MAP in many prairie soils was discussed in the previous Example. Overall, P.bilaji inoculation resulted in an average increase of 73% over uninoculated plots. The increases in plant yield were observed over all the rates of MAP addition, however, this is not surprising since MAP, in the absence of P. BILAJI, was ineffective.

EXAMPLE 12

An experiment was conducted on black Chernozemic soils located at Plum Coolee, Manitoba and at the University of Alberta, Edmonton, Alberta. The soils had a pH of 6.0 (.01M $CaCl_2$) and low levels of available P. Canola (cv Wester) was used as a test crop. Each plot consisted of four treatment rows 7.62 m long separated from the other treatments by a guard (i.e. untreated) row. Rows were spaced 17.8 cm apart.

Florida rock phosphate and commercial monoammonium phosphate (MAP) were used as P sources. The rock phosphate was granulated by heating with urea (140° C.) for eight hours, then cooling the mixture, and sieving out granules with sizes between 1 and 2.5 mm diameter. The final product contained 10% N and 28% $P_2O_5$. Penicillium bilaji inoculum was prepared by growing the fungus on moistened sterile bran at room temperature (20° C.) for one week. The colonized bran was air dried and used directly for application as seed row inoculum. The air-dried bran contained $9 \times 10^{10}$ colony forming units per gram.

Four fertilizer (control, rock phosphate, ½ MAP, MAP) and two fungal treatments (control, P.bilaji) were used in a factorial design with five replications. The full MAP and rock P treatment received 12.2 kgP/ha equivalent, while the ½ MAP treatment received 6.1 kgP/ha, added in the seed row below the seeds. Treatments receiving bran applied P.bilaji received 2.0 g bran per meter of row added in the seed row. Nitrogen as ammonium nitrate was added at a rate equal to 78 kgN/ha at seeding using broadcast methods. All fertilizers, inocula and seeds were added through a mechanical seeder with attachments for adding additional materials.

Two meters of row were harvested from the center of the plots at maturity at Plum Coolee, and 6.0 meters of row were harvested at the University of Alberta. Total and grain weights were measured on oven dried materials from Plum Coolee. Only grain weights were measured at the University of Alberta. The results are shown in Tables 14a and 14b.

TABLE 14a

| Analysis of Canola data, Plum Coolee | | |
|---|---|---|
| | TOTAL DRY MATTER (g/2 m) | GRAIN YIELD (g/2 m) |
| NO P | | |
| — P. bilaji | 221.6 b | 63.8 d |
| + P. bilaji | 292.0 ab | 88.5 abcd |
| ROCK P | | |
| — P. bilaji | 232.3 b | 68.9 cd |
| + P. bilaji | 257.0 ab | 73.7 bcd |
| ½ MAP | | |
| — P. bilaji | 288.0 ab | 94.4 abc |
| + P. bilaji | 315.0 a | 102.9 a |
| MAP | | |
| — P. bilaji | 292.5 ab | 84.8 abcd |
| + P. bilaji | 328.8 a | 96.8 ab |
| Main Effects | | |
| Fertilizer form | | |
| control | 260.7 ab | 77.5 bc |
| rock P | 243.3 b | 71.0 c |
| ½ MAP | 301.5 a | 98.6 a |
| MAP | 310.7 a | 90.8 ab |
| P. bilaji | | |
| — P. bilaji | 260.6 b | 78.8 b |
| + P. bilaji | 300.4 a | 91.4 a |
| Analysis of Variance | | |
| Fert | .05 | .01 |
| P. bilaji | .05 | .05 |
| F*P | ns | ns |

TABLE 14b

| Analysis of Canola data, University of Alberta | |
|---|---|
| | GRAIN YIELD (g/6 m) |
| NO P | |
| — P. bilaji | 508 |
| + P. bilaji | 558 |
| ROCK P | |
| — P. bilaji | 484 |
| + P. bilaji | 614 |
| ½ MAP | |
| — P. bilaji | 443 |
| + P. bilaji | 554 |
| MAP | |
| — P. bilaji | 531 |
| + P. bilaji | 550 |
| Main Effects | |

TABLE 14b-continued

| Analysis of Canola data, University of Alberta | |
|---|---|
| | GRAIN YIELD (g/6 m) |
| Fertilizer form | |
| control | 532a |
| rock P | 556a |
| ½ MAP | 499a |
| MAP | 540a |
| P. bilaji | |
| − P. bilaji | 492a |
| + P. bilaji | 570 b |
| Analysis of Variance | |
| Fert | ns |
| P. bilaji | .01 |
| F*P | ns |

The results show that the addition of P. bilaji to canola crops at the University of Alberta site was able to increase the grain yields by 10% in the absence of added P and to increase grain yields by 25% in the case of the ½ rate of MAP and by 3.6% in the case of the full rate of MAP. At the Plum Coolee site, P. bilaji inoculation increased crop yields of unfertilized plots by 39%, of plots receiving ½ rate of MAP by 9% and of plots receiving the full rate of MAP by 14%. Overall, the main effect of P. bilaji addition at both sites was to increase grain yields by 16% (+P.bilagi/−P.bilaji main effect).

EXAMPLE 13

In this Example, tests were carried out using the strains of P. bilaji deposited as ATCC 22348, ATCC 18309 and ATCC 20851.

Cultures of these strains were inoculated into bottles holding 100 ml 1% glucose-minimal salts media (sterile) containing either Idaho rock phosphate or Florida rock phosphate (0.1 g per bottle) and incubated for 7 days with shaking at 150 rpm. Five replications were carried out for each treatment and at the end of the seven day period the liquid was decanted and replaced with 100 ml of sterile media. The bottles were then incubated for a further seven days. Aliquots of the liquid media were then colorimetrically analyzed for the content of soluble phosphate.

The results are shown in Table 15 below.

TABLE 15

| | Content of soluble phosphate (mg) | | | | | | | |
|---|---|---|---|---|---|---|---|---|
| | ATCC 20851 | | ATCC 18309 | | ATCC 22348 | | UNINOCULATED | |
| Rock Phosphate | 7 days | 14 days | 7 days | 14 days | 7 days | 14 days | 7 days | 14 days |
| IDAHO | 4.44 | 3.69 | 3.56 | 3.88 | 3.66 | 3.97 | 0.10 | 0.73 |
| FLORIDA | 4.79 | 4.44 | 3.76 | 3.90 | 4.38 | 4.30 | 0.11 | 0.52 |
| | TOTAL* | | TOTAL* | | TOTAL* | | TOTAL* | |
| IDAHO | 8.13 | | 7.44 | | 7.63 | | 0.83 | |
| FLORIDA | 9.23 | | 7.66 | | 8.68 | | 0.63 | |

*The TOTAL is the total of the amount of soluble phosphate after 7 days plus that after 14 days.

The results show that phosphate solubilization is an inherent trait of this microorganism and that the novel ATCC 20851 strain is more effective at solubilizing phosphate than the other two ATCC strains.

What I claim is:

1. A method of increasing the availability of phosphorus and/or micronutrients for plant uptake from soil, which method comprises introducing into the soil an inoculum of a strain of the fungus Penicillium bilaji (also known as Penicillium bilaii), said strain being selected from the group consisting of strains identified by the deposit numbers ATCC 22348, ATCC 18309 and ATCC 20851 of the American Type Culture Collection, to release for plant uptake said phosphorus and/or micronutrients from a source thereof selected from the group consisting of sources originally present in the soil, sources added to the soil as amendments and combinations thereof.

2. A method according to claim 1 wherein said source of phophorus and/or micronutrients comprises a source of phosphorus and/or micronutrients native to said soil.

3. A method according to claim 1 wherein a source of phosphorus and/or micronutrients is added to said soil.

4. A method according to claim 3 wherein said source is rock phosphate.

5. A method according to claim 3 wherein said source is a manufactured fertilizer.

6. A method according to claim 5 wherein said manufactured fertilizer is selected from the group consisting of monoammonium phosphate, triple super phosphate, diammonium phosphate, ordinary superphosphate and ammonium polyphosphate.

7. A method according to claim 5 wherein the amount of manufactured fertilizer added to the soil is less than the amount normally employed for soil fertilization.

8. A method according to claim 1, wherein the source of micronutrients is a source of an element selected from the group consisting of copper, iron and zinc.

9. A method according to claim 1, wherein said P. bilaji is introduced in the form of an inoculum supported on a carbon source for the fungus.

10. A method according to claim 1, wherein said P. bilaji is introduced in the form of an inoculum supported on straw.

11. A method according to claim 1, wherein said P. bilaji is introduced in the form of an inoculum supported on bran.

12. A method according to claim 1 wherein said P. bilaji is introduced in the form of an inoculum supported on a carbon source selected from the group consisting of starch, cellulose and mixtures thereof.

13. A method according to claim 1 wherein said P. bilaji is introduced in the form of an inoculum supported in a liquid nutrient medium.

14. A method according to claim 1 wherein said P. bilaji is introduced into the soil in the form of coating on plant seeds, said coating comprising a carrier for said P. bilaji.

15. A method according to claim 14 wherein said carrier is selected from the group consisting of starch, cellulose and mixtures thereof.

16. A method according to claim 15 wherein said carrier comprises bran adhered to said plant seeds.

17. A method according to claim 1 wherein said inoculum is added to the soil in an amount of 0.001–1.0 kg of fungal spores and mycelium (fresh weight) per hectare.

18. A method according to claim 14 wherein said coating comprises $10^2$–$10^6$ colony forming units per seed.

19. A method according to claim 1 wherein said inoculum is added to plant rows in the soil in an amount of up to about $9 \times 10^{10}$ colony forming units per meter of plant row.

20. A method according to claim 1 wherein said P. bilaji introduced into the soil is a strain identified as ATCC 20851.

21. A method according to claim 1 wherein a source of ammonium ion is introduced into the soil.

22. A method according to claim 1 wherein said inoculum is introduced into the soil at a level approximating a root level of plants to be grown in the soil.

23. A method according to claim 1 wherein at least one non-phosphorus containing fertilizer is introduced into the soil.

24. A method according to claim 1 wherein a carbon source for the fungus is added to the soil in addition to said inoculum.

25. A method of increasing the phosphorus uptake plants, which comprises growing the plants in soil containing, in proximity to the plant roots, both a phosphorus source and a strain of the fungus *Penicillium bilaji* (also known as *Penicillium bilaii*), said strain being selected from the group consisting of strains identified by the deposit numbers ATCC 22348, ATCC 18309 and ATCC 20851 of the American Type Culture Collection.

26. A method according to claim 25 wherein the plants are crop plants.

27. A method according to claim 25 wherein the plants are wheat plants.

28. A method according to claim 25 wherein the plants are bean plants.

29. A composition for application to soil, which comprises:
an inoculum of a strain of the fungus *Penicillium bilaji* (also known as *Penicillium bilaii*), said strain being selected from the group consisting of strains identified by the deposit numbers ATCC 22348, ATCC 18309 and ATCC 20851 of the American Type Culture Collection, and a soil-compatible carrier for the fungus.

30. A composition according to claim 29 wherein *P. bilaji* is a strain identified as ATCC 20851.

31. A composition according to claim 29 wherein said soil-compatible carrier is selected from the group consisting of amended wheat straw, bran, starch, cellulose and mixtures thereof.

32. A composition according to claim 29 wherein said soil-compatible carrier comprises a liquid containing a nutrient for the fungus.

33. A composition according to claim 29 in the form of a coating for plant seeds.

34. A composition according to claim 29 which further includes a solid particulate rock phosphate.

35. A composition according to claim 29 which further comprises a source of ammonium ion.

36. A strain of *Penicillium bilaji* identified as ATCC 20851.

37. A plant seed having a coating comprising an inoculum of a strain of the fungus *P. bilaji* (also known as *Penicillium bilaii*), said strain being selected from the group selected from strains identified by the deposit numbers ATCC 22348, ATCC 18309 and ATCC 20851 of the American Type Culture Collection, and a solid soil-compatible carrier therefor.

38. A plant seed according to claim 37 wherein the *P. bilaji* is a strain identified as ATCC 20851.

39. A plant seed according to claim 37 wherein the carrier is selected from the group consisting of starch, cellulose and mixtures thereof.

40. A plant seed according to claim 37 wherein said carrier comprises bran flakes adhered to said seeds.

* * * * *